United States Patent
Platzek et al.

(10) Patent No.: US 6,831,164 B2
(45) Date of Patent: Dec. 14, 2004

(54) PROCESS FOR THE PRODUCTION OF PERACYLATED 1-0-GLYCOSIDES

(75) Inventors: Johannes Platzek, Berlin (DE); Klaus-Dieter Graske, Berlin (DE); Ulrich Niedballa, Berlin (DE)

(73) Assignee: Schering Aktiengesellschaft, Berlin (DE)

(*) Notice: Subject to any disclaimer, the term of this patent is extended or adjusted under 35 U.S.C. 154(b) by 0 days.

(21) Appl. No.: 10/192,856

(22) Filed: Jul. 11, 2002

(65) Prior Publication Data

US 2003/0069402 A1 Apr. 10, 2003

Related U.S. Application Data

(60) Provisional application No. 60/305,876, filed on Jul. 18, 2001.

(51) Int. Cl.$^7$ .................. C07H 15/00; C07H 17/00; C07G 11/00; C07G 3/00
(52) U.S. Cl. .................. 536/4.1; 536/18.5; 536/18.6; 536/124
(58) Field of Search .................. 536/18.5, 4.1, 536/18.6, 124

(56) References Cited

U.S. PATENT DOCUMENTS

| | | | |
|---|---|---|---|
| 5,854,408 A | * 12/1998 | Mandai et al. | 536/18.6 |
| 6,545,135 B2 | * 4/2003 | Platzek et al. | 536/17.4 |
| 2002/0022742 A1 | 2/2002 | Platzek et al. | |

FOREIGN PATENT DOCUMENTS

| | | |
|---|---|---|
| EP | 0 882733 A1 * | 9/1998 |
| EP | 0 882 733 A | 12/1998 |
| EP | 0 882 733 | 12/1998 |
| JP | 6-271597 | 9/1994 |
| JP | 6271597 A | 9/1994 |
| WO | WO 88 00592 A | 1/1988 |
| WO | WO 96/35700 | 11/1996 |
| WO | WO 01 68659 A | 9/2001 |

OTHER PUBLICATIONS

T. Sugawara et al., "Synthesis of Omega–(Methoxycarbonyl)Alkyl and 9–(Methoxycarbonyl)–3,6–Dioxanonyl Glycopyranosides for the Preparation of Carbohydrate–Protein Conjugates," Carbohydrate Research, Elsevier Scientific Publishing Company, Amsterdam, NL, Bd. 230, Nr. 1, 1992, pp. 117–150, XP001018683.

R. R. Schmidt: "1–0–Alkylation of D–Glucopyranose," Journal of Carbohydrate Chemistry, New York, NY, US, Bd. 3, Nr. 1, 1984, pp. 67–84, XP001021740.

Database WPI, Section Ch, Week 199443 Derwent Publications Ltd., London, GB; AN 1994–347142, XP002226505 & JP 06 27 1597 A (DDS Kenkyusho KK), Sep. 27, 1994.

Oswald Lockhoff: "An Access to Glycoconjugate Libraries Through Multicomponent Reactions," Angewandte Chemie. International Edition, Verlag Chemie. Weinheim, DE, Bd. 37, Nr. 24, 1998, pp. 3436–3439, XP002171115.

* cited by examiner

Primary Examiner—James O. Wilson
Assistant Examiner—Traviss C. McIntosh, III
(74) Attorney, Agent, or Firm—Millen, White, Zelano, Branigan, P.C.

(57) ABSTRACT

The invention relates to a process for the production of peracylated 1-O-glycosides of general formula I or salts thereof

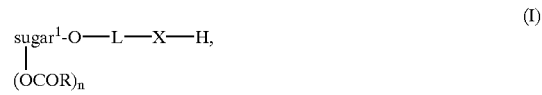

(I)

in which sugar$^1$ is a monosaccharide that is functionalized in 1-OH-position,

R represents methyl, ethyl, propyl, isopropyl, tbutyl, phenyl, n means 2, 3 or 4, X means —COO— or —NH—and L means a straight-chain, branched, saturated or unsaturated $C_1$–$C_{30}$ carbon chain, which optionally is interrupted or substituted by groups.

The process according to the invention starts from economical starting materials, provides good yields and allows the production of peracylated saccharides with 1-O-functionalized side chains on an enlarged scale.

18 Claims, No Drawings

PROCESS FOR THE PRODUCTION OF PERACYLATED 1-0-GLYCOSIDES

This application claims the benefit of the filing date of U.S. Provisional Application Ser. No. 60/305,876 filed Jul. 18, 2001.

The invention relates to a new process for the production of peracylated 1-O-glycosides of general formula I, which is cited in more detail in the claims. The process according to the invention starts from economical starting materials, provides good yields, and allows the production of peracylated saccharides with 1-O-functionalized side chains on an enlarged scale.

Peracylated saccharide derivatives are valuable intermediate products in synthetic chemistry. Pharmaceutical chemistry primarily uses such components very frequently, since many highly potent and selective pharmaceutical agents carry sugar radicals. Thus, for example, in the Journal of Drug Targeting 1995, Vol. 3, pp. 111–127, applications of the so-called "glycotargeting" are described. So-called "multi-antennary sugar chains" are described in Chemistry Letters 1998, p. 823. By clustering sugar units, the carbohydrate-receptor-interaction in the case of the cell-cell-interaction is considerably improved. The synthesis of galactosides with high affinity to the asialoglycoprotein receptor was published in J. Med. Chem. 1995, 38, p. 1538 (see also Int. J. Peptide Protein Res. 43, 1994, p. 477). Here, derivatized galactoses with functionalized side chains are produced, which then can be suspended on various other molecules. A good survey on the use of saccharides as a basis of glycobiology was provided in Acc. Chem. Res. 1995, 321. Also, for the synthesis of LewisX mimetic agents (Tet. Lett. Vol. 31, 5503), functionalized monosaccharides are used as precursors (see also JACS 1996, 118, 6826).

The use of derivatized monosaccharides as intermediate stages for potential pharmaceutical agents was well represented in Current Medicinal Chemistry, 1995, 1, 392. Perbenzylated-1-OH-sugar derivatives (galactose, glucose) are also used in the synthesis of heart-active glycosides (digitoxin-conjugates). The 1-O-glycosylation is carried out here via trichloroacetimidate and $BF_3$-catalysis (J. Med. Chem. 1986, 29, p. 1945). For the production of immobilized sugar ligands (e.g., linkage to HSA), functionalized, protected monosaccharides are used (Chemical Society Reviews 1995, p. 413).

It is the purpose of a group of syntheses to introduce additional functionality into a sugar molecule via a 1-O-glycosylation reaction. Here, primarily terminal COOH—, amino- or OH— groups are of interest, since the latter can be further reacted in subsequent steps.

The production of 1-O-glycosides is carried out in most cases according to standard methods, such as, e.g., according to the trichloroacetimidate methods described by Koenigs-Knorr, Helferich or by R. R. Schmidt [W. Koenigs and E. Knorr, Ber. dtsch. chem. Ges. 34 (1901) 957; B. Helferich and J. Goendeler, Ber. dtsch. Chem. Ges. 73, (1940) 532; B. Helferich, W. Piel and F. Eckstein, Chem. Ber. 94 (1961), 491; B. Helferich and W. M. Müller, Chem. Ber. 1970, 103, 3350; G. Wulff, G. Röhle and W. Krüger, Ang. Chem. Internat. Edn., 1970, 9, 455; J. M. Berry and G. G. S. Duthon, Canad. J. Chem. 1972, 50, 1424; R. R. Schmidt, Angew. Chem. [Applied Chemistry] 1986, 98, 213.]

A feature that is common to all of these methods is that the 1-hydroxyl group is converted into a reactive form that is ultimately used as a leaving group. Under Lewis acid catalysis (partially in stoichiometric amount), the actual reaction is carried out with an alcohol to form 1-O-glycoside. For such reactions, numerous examples are provided in the literature.

In the production of immunostimulant KRN-7000 (Kirin Brewery), the condensation of tetra-O-benzyl-β-D-galactopyranosyl-bromide with a primary alcohol, whose hydroxyl group sits at the end of a di-hydroxy-amido-C-chain (in DMF/toluene under Lewis acid catalysis), is thus a central step (Drug of the Future 1997, 22(2), p. 185). In Japanese Patent JP 95-51764, the reaction of 1-O-acetyl-2,3,4-tri-O-benzyl-L-fucopyranose with polyoxyethylene-30-phytosterol (BPS-30, NIKKO Chem., Japan) under trimethyl-silylbromide/zinc triflate catalysis was described. In Bull. Chem. Soc. 1982, 55(4), pp. 1092–6, 1-O-glycosylations of perbenzyl-sugars under titanium tetrachloride catalysis in dichloromethane are described.

In Liebigs Ann. Org. Bioorg. Chem.; EN; 9; 1995; 1673–1680, the production of 3,4,5-trisbenzyloxy-2-benzyloxymethyl-6-(2-hexadecyloxyethoxy)-tetrahydropyran is described. Starting from 2,3,4,6-tetra-O-benzyl-D-glucopyranose, the 1-O-glycosylation is performed with use of $Bu_4NBr$, $CoBr_2$, $Me_3SiBr$ and a molecular sieve in methylene chloride within 60 hours.

A tetrabenzyl derivative, which contains a terminal carboxyl group that is protected as a methyl ester, is described in Carbohydr. Res.; EN; 230; 1; 1992; 117. The carboxyl group can then be released and further reacted. For glycosylation, silver carbonate is used in dichloromethane. The use of expensive silver carbonate limits the batch size and makes an economical up-scaling almost impossible. The same problem applies for the compound below, which was described in Tetrahedron Lett. 30, 44, 1989, p. 6019. Here, 2,3,4,6-tetra-O-benzyl-D-mannosyl-bromide in nitromethane is reacted with 2-benzyloxyethanol with the aid of mercury cyanide to form 1-O-glycoside. The use of mercury cyanide in pilot-plant installations is problematical in nature and can be rejected from the environmental-political standpoint.

The substance libraries for the high-capacity-screening described most recently very frequently use saccharides (Angew. Chemie 1995, 107, 2912). Here, the purpose is to have present sugar components in protected form, which carry a functional group, such as, e.g., —COOH, or —$NH_2$, which can be reacted in, e.g., an automated synthesis. The components that are used in this respect were described by Lockhoff, Angew. Chem. 1998, 110 (24), p. 3634. Primarily the 1-O-acetic acid of perbenzyl-glucose is important here. The production is carried out over two stages, via trichloroacetimidate and reaction with hydroxyacetic acid ethyl ester, $BF_3$ catalysis in THF and subsequent saponification with NaOH in MeOH/THF. The total yield over two stages is only 59%, however.

In the same publication, the production of a 1-O-(aminoethyl)-glycoside of the perbenzylated glucose is also described. The reaction is carried out, also starting from trichloroacetimidate, by reaction with N-formylaminoethanol under BF3-catalysis in THF and subsequent saponification in MeOH/THF. The total yield is also relatively low here; it is 45%.

A 1-O-(aminoethyl) derivative of perbenzylxylose passes through as an intermediate product in Carbohydrate Research 1997, 298, p. 173. The synthesis is very lengthy, however, since it starts from 1-bromo-peracetate of xylose. The actual 1-O-glycosylation is carried out via a 1-phenylthioether, which is reacted with 2-azidoethanol under DMTST catalysis (=dimethyl (methylthio)-sulfonium-triflate) in dichloromethane (total number of stages: 7). The total yield is not suitable for an industrial application with less than 40%.

In the survey article by R. R. Schmidt in Angew. Chem. 1986, 98, pp. 213–236, direct reactions of 1-OH-perbenzyl-glucose and -ribose with 2-haloesters and triflates are described. As a base, sodium hydride in THF or benzene is used (Chem. Ber. 1982, 115); the yields are between 40 and 55%. The use of sodium hydride in dioxane or potassium-tert-butylate in THF (both at room temperature) is also described for 1-O-alkylation with triflates (Angew. Chem. 1986, 98, p. 218). The anhydrous reaction conditions that are to be followed most strictly represent a large hurdle in up-scaling such alkylations.

All processes known to date have the great disadvantage that an up-scaling of the process cannot be achieved easily. The use of Lewis acids in 1-O-glycosylation as well as sodium hydride in 1-O-alkylation already requires anhydrous reaction conditions, which in large batches is always associated with difficulties. The working-up and disposal of reaction adjuvants (Hg/cyanide/etc.) is also a problem in many cases.

The object of the invention was therefore to provide a process with which peracylated saccharides with 1-O-functionalized side chains can be produced at a reasonable price and in an ecologically beneficial way on an enlarged scale.

The object of the invention is achieved according to the process that is indicated in the claims, with which peracylated 1-O-glycosides of general formula I

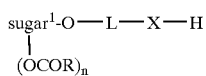

can be produced. According to the definition of the invention, $sugar^1$ in general formula I means a monosaccharide that is functionalized in 1-OH position, whereby in this connection, it can also be a deoxy sugar, which contains an H-atom instead of one or more OH groups. In a preferred embodiment of the invention, the sugar in general formula I means a monosaccharide with 5 or 6 C atoms, e.g., glucose, mannose, galactose, ribose, arabinose or xylose or deoxy sugars thereof, such as, for example, 6-deoxygalactose (fucose) or 6-deoxy-mannose (rhamnose).

Radical —COR represents the acyl group that is present in at least two places based on the monosaccharide that is used or its deoxy form, and is present accordingly in several places with use of di-, tri- or polysaccharides. As radicals R, aliphatic and aromatic groups, such as, for example, methyl, ethyl, isopropyl, t-butyl or phenyl are considered.

Radical X means —COO— or —NH—. In the result of the process according to the invention, alcohols, carboxylic acids, or amines of general formula I are thus obtained.

Radical L can mean a straight-chain, branched, saturated, or unsaturated $C_1$–$C_{30}$-carbon chain, which optionally is interrupted by 1–10 oxygen atoms, 1–3 sulfur atoms; 1–2 phenylene groups, 1–2 phenylenoxy groups, 1–2 phenylene-dioxy groups; a thiophene radical, pyrimidine radical or pyridine radical; and/or optionally is substituted with 1–3 phenyl groups, 1–3 carboxyl groups, 1–5 hydroxy groups, 1–5 O—$C_1$–$C_7$ alkyl groups, or 1–3 amino groups; 1–3 CF 1–10 fluorine atoms. In terms of the invention, preferred radicals L are

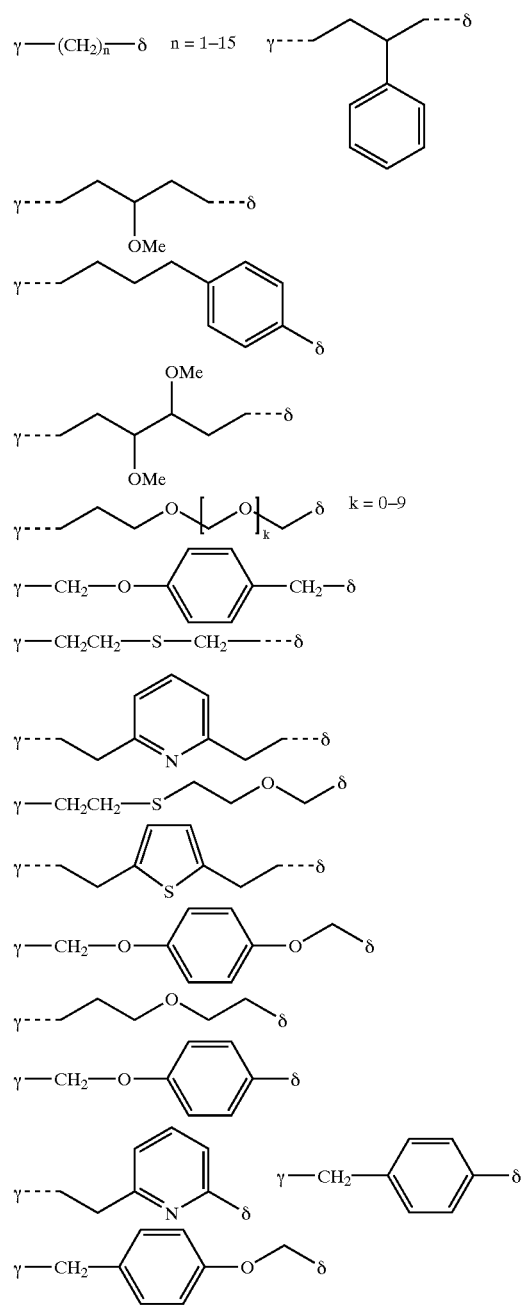

whereby γ means the interface site to the sugar, and δ is the interface site to radical X. An especially preferred linker L is the —$CH_2$ group.

For the production of peracylated 1-O-glycosides of general formula I, a peracylated 1-OH sugar of general formula II $$sugar^1\text{-OH,} \\ | \\ (OCOR)_n$$

(II)

in which sugar, R and n have the above-indicated meaning, is dissolved in an organic solvent and reacted with an alkylating reagent of general formula III

(III), in which Nu means a nucleofuge, L and X have the above-mentioned meaning, and Sg is a protective group, in the presence of a base and optionally a phase transfer catalyst. As a nucleofuge, for example, the radicals —Cl, —Br, —I, —OTs, —OMs, —OSO$_2$CF$_3$, —OSO$_2$C$_4$F$_9$ or —OSO$_2$C$_8$F$_{17}$ can be contained in the alkylating reagent of general formula III.

Protective group Sg is a common acid or amine protective group, depending on whether X means the radical —COO— or —NH—. These protective groups are well known to one skilled in the art (Protective Groups in Organic Syntheses, Second Edition, T. W. Greene and P. G. M. Wuts, John Wiley & Sons, Inc., New York 1991).

The reaction according to the invention can be carried out at temperatures of 0–50° C., preferably 0° C. to room temperature. The reaction times are 10 minutes to 24 hours, preferably 20 minutes to 12 hours.

The base is added either in solid form, preferably in fine-powder or liquid form. Cesium carbonate, potassium carbonate, 1,8-diazabicyclo-[5.4.0]undec-7-ene (DBU), 1,5-diazabicyclo-[2.2.2]octane (DBN), 1,4-diaza-bicyclo[2.2.2]octane (DABCO), potassium-t-butoxide and sodium-t-butoxide, sodium carbonate, or a mixture that consists of cesium carbonate and potassium carbonate or sodium carbonate are used as preferred bases.

As organic solvents, for example, acetonitrile, dioxane, tetrahydrofuran, diethoxymethane, 1,2-dimethoxyethane, diethylene glycol dimethyl ether, benzene, formamide, hexane, toluene, dimethylformamide, dimethylacetamide, cyclohexane, CF3-benzene, diethyl ether, dichloromethane, methyl-t-butyl ether (MTB), dimethyl sulfoxide, sulfolane or mixtures thereof can be used in the alkylating process according to the invention.

As phase transfer catalysts, the quaternary ammonium or phosphonium salts that are known for this purpose or else crown ethers, such as, e.g., [15]-crown 5 or [18]-crown 6, are used in the process according to the invention. Preferably quaternary ammonium salts with four hydrocarbon groups that are the same or different on the cation, selected from methyl, ethyl, propyl, isopropyl, butyl or isobutyl, are suitable. The hydrocarbon groups on the cation must be large enough to ensure good solubility of the alkylating reagent in the organic solvent. According to the invention, N(butyl)$_4^+$-Cl$^-$, or N(butyl)$_4^+$-HSO$_4^-$, but also N(methyl)$_4^+$-Cl$^-$ is especially preferably used.

After the reaction is completed, the working-up of the reaction mixture can be carried out by isolation of the still protected end product and subsequent usual cleavage of the protective group to the end product of general formula I. It is preferred, however, not to isolate the still protected end product but rather to remove the solvent, to take up the residue in a new solvent that is suitable for the cleavage of the protective group and to perform the cleavage here. The procedure for cleavage of the protective group and for regeneration of the acid, amino or hydroxy group is well known to one skilled in the art.

If, for example, protective group Sg is an acid protective group that blocks the acid proton of the carboxy group, thus, e.g., methyl, ethyl, benzyl or tert-butyl, the acid is usually regenerated by alkaline hydrolysis. In the process of the invention, however, the alcoholic hydroxyl groups are also protected as esters. As a protective group for the carboxylic acid in addition to the allyl group and silyl group, the benzyl group is available. This protective group can be easily removed by catalytic hydrogenation. As a catalyst, in this case palladium (10%) on activated carbon has proven to be effective.

As hydroxy protective groups (in L), e.g., benzyl, 4-methoxybenzyl, 4-nitrobenzyl, trityl, diphenylmethyl, trimethylsilyl, dimethyl-tert-butylsilyl, or diphenyl-tert-butylsilyl groups are suitable.

The hydroxy groups can also be present, e.g., as THP-ethers, α-alkoxyethylethers, MEM-ethers or as esters with aromatic or aliphatic carboxylic acids, such as, e.g., acetic acid or benzoic acid. In the case of polyols, the hydroxy groups can also be protected in the form of ketals with, e.g., acetone, acetaldehyde, cyclohexanone or benzaldehyde.

The hydroxy protective groups can be released according to the literature methods that are known to one skilled in the art, e.g., by hydrogenolysis, acid treatment of ethers and ketals, alkali treatment of esters or treatment of silyl protective groups with fluoride (see, e.g., Protective Groups in Organic Syntheses, Second Edition, T. W. Greene and P. G. M. Wuts, John Wiley & Sons, Inc., New York, 1991).

The NH$_2$ groups can be protected and released again in a variety of ways. The N-trifluoroacetyl derivative is cleaved by potassium or sodium carbonate in water [H. Newman, J. Org. Chem., 30:287 (1965), M. A. Schwartz et al., J. Am. Chem. Soc., 95 G12 (1973)] or simply by ammonia solution [M. Imazama and F. Eckstein, J. Org. Chem., 44:2039 (1979)]. The tert-butyloxycarbonyl derivative is equally easy to cleave: stirring with trifluoroacetic acid suffices [B. F. Lundt et al., J. Org. Chem., 43:2285 (1978)]. The group of NH$_2$-protective groups to be cleaved hydrogenolytically or reductively is very large: The N-benzyl group can be cleaved easily with hydrogen/Pd—C [W. H. Hartung and R. Simonoff, Org. Reactions VII, 263 (1953)], which also applies for the trityl group [L. Zervas, et al., J. Am. Chem. Soc., 78:1359 (1956)] and the benzyloxycarbonyl group [M. Bergmann and L. Zervas Ber. 65:1192 (1932)].

Of the silyl derivatives, the easily cleavable tert-butyldiphenylsilyl compounds [L. E. Overman et al., Tetrahedron Lett., 27:4391 (1986)] and the 2-(trimethylsilyl)-ethyl carbamates [L. Grehn et al., Angew. Chem. Int. Ed. Engl., 23:296 (1983)] and the 2-trimethylsilylethanesulfonamides [R. S. Garigipati and S. M. Weinreb, J. Org. Chem., 53:4134 (1988)] are used, which can be cleaved with fluoride ions. Especially easily cleavable is the 9-fluorenylmethyl-carbamate: The cleavage is carried out with amines such as piperidine, morpholine, 4-dimethylaminopyridine, but also with tetrabutylammonium fluoride [L. A. Corpino et al., J. Org. Chem., 55:1673 (1990); M. Ueki and M. Amemiya, Tetrahedron Lett., 28:6617 (1987)].

The isolation of the end product of general formula I (amine or carboxylic acid) that is obtained is also carried out according to methods that are commonly used and well known to one skilled in the art.

Thus, for example, in the case of the acid protective group, the solvent is evaporated from the hydrolysis reaction, and the residue is taken up in an aprotic solvent. By acidification with an aqueous acid solution, the pH is set at about 2–4, and then the organic phase is separated. Using crystallization or chromatography, the peracylated 1-O-glycoside can now be obtained.

The compounds of general formula I that are obtained optionally also can be converted into their salts in the usual way.

The yields of the compounds of general formula I, which can be achieved with the process according to the invention, are good. For known compounds in which a comparison with the prior art is possible, they exceed the yields of the prior art. Thus, for example, (WO 96/35700), in the reaction of acetobromoglucose with glycolic acid methyl ester under the influence of mercury oxide and mercury(II) bromide according to Koenigs-Knorr, the 1-O-methyloxycarbonylmethyl-2,3,4,6-tetra-O-acetyl-glucopyranose is obtained with a yield of 60%. The saponification to the free acid would be connected with a further loss in yield. EP 882733 also describes the production of this compound, but without yield information. According to the process of the invention, the acid is also obtained in a two-stage process. Here, the yield is 78%, however (Example 24 of this application).

The corresponding benzyloxycarbonylmethyl-2,3,4,6-O-tetraacetyl-galactopyranose is described in JP 6-271597.

In addition to the high yields, the process according to the invention also offers the advantage that it starts from economical starting materials, makes possible a scale-up of the process, and allows an easy isolation of the end products.

The starting materials are commercially available products or can be obtained easily from commercially available precursors. Tetra-2,3,4,6-O-acetyl-D-glucopyranose thus can be easily obtained from the pentaacetyl compound by partial hydrolysis with benzylamine (Organikum, 4th Edition, VEB Deutscher Verlag der Wissenschaften Berlin 1964, p. 376). In the case of Fluka, methyl-D-mannopyranoside and methyl-D-galactopyranoside are catalog items. By acylation and cleavage of the glycoside, 2,3,4,6-tetra-O-acyl-D-mannose or -galactose can be obtained.

The peracyl-1-OH derivatives of the pentoses (ribose, arabinose), hexoses and deoxyhexoses (rhamnose, fucose) can be obtained via the sequence of methylglycoside-peracyl-methylglycoside-peracyl-1-OH-saccharide.

The compounds that are produced according to the invention are valuable intermediate products in synthetic chemistry. They can thus be used, for example, in the synthesis of carbohydrate dendrimers, for synthesis of NMR contrast media and for introducing sugar radicals into pharmaceutical agents.

The process according to the invention is to be explained in more detail below in the embodiments.

The entire disclosures of all applications, patents and publications, cited herein and of corresponding German application No. 10135098.8, filed Jul. 11, 2001, and U.S. Provisional Application Serial No. 60/305,876, filed Jul. 18, 2001, are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

2,3,4,6-Tetra-O-acetyl-1-O-carboxymethyl-mannopyranose

A mixture that consists of 34.83 g (100 mmol) of 2,3,4,6-tetra-O-acetyl-mannopyranose, 1.70 g (5 mmol) of tetrabutylammonium hydrogen sulfate and 82.93 g (600 mmol) of fine-powder potassium carbonate in 350 ml of dioxane is cooled to 0° C. At 0° C., 34.36 g (150 mmol) of bromoacetic acid benzyl ester is added in drops over 10 minutes while being stirred vigorously. It is stirred for one hour at 0° C. 250 ml of MTB (methyl-tert-butyl ether) is added, solid is filtered out, and the filtrate is evaporated to the dry state in a vacuum. The residue is taken up in 500 ml of ethanol. 5 g of palladium (10%) on activated carbon is added thereto and hydrogenated until no more hydrogen is taken up by the solution. Catalyst is filtered out, it is rewashed with ethanol, and the combined solutions are evaporated to the dry state in a vacuum.

The residue is chromatographed on silica gel (mobile solvent: dichloromethane/nhexane/ethanol/acetic acid= 20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 34.5 g (85% of theory, over two stages) of a colorless, viscous oil Elementary Analysis: Cld: C 47.29 H 5.46 Fnd: C 47.38 H 5.55

EXAMPLE 2

2,3,4,6-Tetra-O-benzoyl-1-O-carboxymethyl-mannopyranose

A mixture that consists of 59.66 g (100 mmol) of 2,3,4,6-tetra-O-benzoyl-mannopyranose, 1.7 g (5 mmol) of tetrabutylammonium hydrogen sulfate and 63.59 g (600 mmol) of fine-powder sodium carbonate in 350 ml of 1,2-dimethoxyethane is cooled to 0° C. At 0° C., 34.36 g (150 mmol) of bromoacetic acid benzyl ester is added in drops over 10 minutes while being stirred vigorously. It is stirred for one hour at 0° C. 250 ml of MTB (methyl-tert-butyl ether) is added, solid is filtered out, and the filtrate is evaporated to the dry state in a vacuum. The residue is dissolved in 500 ml of ethanol. 5 g of palladium (10%) on activated carbon is added thereto and hydrogenated until hydrogen absorption is completed. Then, catalyst is filtered out, rewashed with ethanol, and the combined solutions are evaporated to the dry state in a vacuum. The residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 53.03 g (81% of theory, over two stages) of a colorless, viscous oil Elementary Analysis: Cld: C 66.05 H 4.62 Fnd: C 66.19 H 4.78

EXAMPLE 3

2,3,4,6-Tetra-O-pivaloyl-1-O-(5-carboxypentyl)-mannopyranose

A mixture that consists of 51.66 g (100 mmol) of 2,3,4,6-tetra-O-pivaloyl-mannopyranose, 0.55 g (5 mmol) of tetramethylammonium chloride and 82.93 g (600 mmol) of fine-powder potassium hydroxide in 350 ml of diethylene glycol dimethyl ether is cooled to 10° C. At 10° C., 35.7 g (150 mmol) of 6-bromohexanoic acid benzyl ester is added in drops within 10 minutes while being stirred vigorously. It is stirred for two hours at 10° C. 250 ml of MTB (methyl-tert-butyl ether) is added, solid is filtered out, and the filtrate is evaporated to the dry state in a vacuum. The residue is taken up in 500 ml of ethanol, mixed with 5 g of palladium (10%) on activated carbon and hydrogenated until hydrogen absorption is completed. Catalyst is filtered out, rewashed with ethanol, and the combined solutions are evaporated to the dry state in a vacuum. The residue is chromatographed on silica gel (mobile solvent: dichloromethane/n=hexane/ ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 49.83 g (79% of theory, over two stages) of a colorless solid Elementary Analysis: Cld: C 60.93 H 8.63 Fnd: C 61.12 H 8.78

EXAMPLE 4

2,3,4,6-Tetra-O-acetyl-1-O-(1-phenyl-1-carboxy-eth-2-yl)-mannopyranose

A mixture that consists of 34.83 g (100 mmol) of 2,3,4,6-tetra-O-acetyl-mannopyranose, 1.39 g (5 mmol) of tetrabutylammonium chloride and 35.8 g (110 mmol) of fine-powder cesium carbonate in 400 ml of dioxane is cooled to 0° C. At 0° C., 47.88 g (150 mmol) of 2-phenyl-3-bromopropionic acid-benzyl ester, dissolved in 30 ml of dioxane, is added in drops over 10 minutes while being stirred vigorously. It is stirred for one hour at 0° C. 250 ml of MTB (methyl-tert-butyl ether) is added, solid is filtered out, and the filtrate is evaporated to the dry state in a vacuum. The residue is taken up in 500 ml of tetrahydrofuran. 5 g of palladium (10%) on activated carbon is added thereto and hydrogenated until hydrogen absorption is completed. Then, catalyst is filtered out, it is rewashed with a little tetrahydrofuran, the organic solutions are combined, and it is evaporated to the dry state in a vacuum. The residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 39.22 g (79% of theory, over two stages) of a colorless solid Elementary Analysis: Cld: C 55.64 H 5.68 Fnd: C 55.81 H 5.84

EXAMPLE 5

2,3,4,6-Tetra-O-benzoyl-1-O-carboxymethyl-mannopyranose

A mixture that consists of 59.66 g (100 mmol) of 2,3,4,6-tetra-O-benzoyl-mannopyranose, 1.39 g (5 mmol) of tetrabutylammonium chloride and 15.2 g (110 mmol) of anhydrous potassium carbonate in 500 ml of dimethylformamide is cooled to 0° C. At 0° C., 36.92 g (200 mmol) of chloroacetic acid benzyl ester is added in drops over 20 minutes while being stirred vigorously. It is stirred for one hour at 10° C. 250 ml of methyl-tert-butyl ether is added, the organic phase is separated, it is filtered and evaporated to the dry state in a vacuum. The residue is taken up in 500 ml of ethanol and mixed with 5 g of palladium (10%) on activated carbon. It is hydrogenated until hydrogen absorption is completed. Catalyst is filtered out, it is rewashed with a little ethanol, and the combined solutions are evaporated to the dry state in a vacuum. The residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 53.82 g (82% of theory, over two stages) of a colorless, viscous oil Elementary Analysis: Cld: C 66.05 H 4.62 Fnd: C 66.21 H 4.73

EXAMPLE 6

2,3,4,6-Tetra-O-acetyl-1-O-(4-carboxybutyl)-glucopyranose

A mixture that consists of 34.83 g (100 mmol) of 2,3,4,6-tetra-O-acetyl-glucopyranose, 1.39 g (5 mmol) of tetrabutylammonium chloride and 15.22 g (100 mmol) of DBU in 300 ml of tetrahydrofuran is cooled to 0° C. At 0° C., 54.37 g (150 mmol) of 5-tosyloxy-pentanecarboxylic acid benzyl ester, dissolved in 40 ml of tetrahydrofuran, is added in drops over 30 minutes while being stirred vigorously. It is stirred for three hours at 0° C. 300 ml of MTB (methyl-tert-butyl ether) is added, solid is filtered out, and the filtrate is evaporated to the dry state in a vacuum. The residue is taken up in 500 ml of tetrahydrofuran. 5 g of palladium (10%) on activated carbon is added thereto and hydrogenated until hydrogen absorption is completed. Then, catalyst is filtered out, it is rewashed with a little tetrahydrofuran and evaporated to the dry state in a vacuum. The residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate, and shaken out three times with 200 ml of water. Then, the organic phase is separated and evaporated to the dry state in a vacuum.

Yield: 34.98 g (78% of theory, over two stages) of a colorless solid Elementary Analysis: Cld: C 50.89 H 6.29 Fnd: C 51.02 H 6.41

EXAMPLE 7

2,3,4,6-Tetra-O-pivaloyl-1-O-carboxymethyl-glucopyranose

A mixture that consists of 54.1 g (100 mmol) of 2,3,4,6-tetra-O-pivaloyl-glucopyranose, 1.39 g (5 mmol) of tetrabutylammonium chloride and 11.22 g of potassium-t-butoxide (100 mmol) in 500 ml of dimethylacetamide is cooled to 0° C. At 0° C., 34.36 g (150 mmol) of bromoacetic acid benzyl ester is added in drops over 20 minutes while being stirred vigorously. It is stirred for 0.5 hour at 0° C. 250 toluene is added, the organic phase is separated, it is filtered, and it is evaporated to the dry state in a vacuum. The residue is taken up in 400 ml of methanol, mixed with 5 g of palladium (10%) on activated carbon and hydrogenated until hydrogen absorption is completed. Catalyst is filtered out, it is rewashed with a little methanol, and the combined organic solutions are evaporated to the dry state in a vacuum. The residue is chromatographed on silica gel (mobile solvent: dichloromethane/n-hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 47.12 g (82% of theory, over two stages) of a colorless, viscous oil

Elementary Analysis: Cld: C 58.52 H 8.07 Fnd: C 58.69 H 8.19

EXAMPLE 8

2,3,4,6-Tetra-O-acetyl-1-O-(10-carboxydecyl)-glucopyranose

A mixture that consists of 34.83 g (100 mmol) of 2,3,4,6-tetra-O-acetylglucopyranose, 0.55 g (5 mmol) of tetramethylammonium chloride and 12.42 g (100 mmol) of DBN in 350 ml of benzene is cooled to 0° C. At 0° C., 53.30 g (150 mmol) of 11-bromoundecanoic acid benzyl ester, dissolved in 50 ml of benzene, is added in drops over 30 minutes while being stirred vigorously. It is stirred for two hours at 20° C. 250 ml of methyl-tert-butyl ether is added, solid is filtered out, and the filtrate is evaporated to the dry state in a vacuum. The residue is taken up in 500 ml of ethanol. 5 g of palladium (10%) on activated carbon is added thereto and hydrogenated until hydrogen absorption is completed. Catalyst is filtered out, it is rewashed with a little ethanol, and the combined solutions are evaporated to the dry state in a vacuum. The residue is chromatographed on silica gel (mobile solvent: dichloromethane/n-hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 41.54 g (78% of theory, over two stages) of a colorless solid Elementary Analysis: Cld: C 56.38 H 7.57 Fnd: C 56.42 H 7.81

EXAMPLE 9
2,3,4,6-Tetra-O-acetyl-1-O-carboxymethyl-galactopyranose

A mixture that consists of 34.83 g (100 mmol) of 2,3,4,6-tetra-O-acetyl-mannopyranose, 1.39 g (5 mmol) of tetrabutylammonium chloride and 9.62 g (100 mmol) of sodium-t-butoxide in 350 ml of dimethyl sulfoxide is cooled to 0° C. At 0° C., 36.92 g (200 mmol) of chloroacetic acid benzyl ester is added in drops over 20 minutes while being stirred vigorously. It is stirred for one hour at 10° C. 250 ml of methyl-tert-butyl ether is added, the organic phase is separated, and it is filtered. The solvent is distilled off in a vacuum. The residue is taken up in 500 ml of ethanol. 5 g of palladium (10%) on activated carbon is added thereto and hydrogenated until hydrogen absorption is completed. Catalyst is filtered out, it is rewashed with a little ethanol and evaporated to the dry state in a vacuum. The residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 33.32 g (82% of theory, over two stages) of a colorless, viscous oil Elementary Analysis: Cld: C 47.29 H 5.46 Fnd: C 47.38 H 5.57

EXAMPLE 10
2,3,4,6-Tetra-O-acetyl-1-O-[1-(4-carboxy)-phenyl-prop-3-yl-galactopyranose A mixture that consists of 34.83 g (100 mmol) of 2,3,4,6-tetra-O-acetylgalactopyranose, 1.39 g (5 mmol) of tetrabutylammonium chloride and 67.31 g (600 mmol) of 1,4-diazabicyclo[2.2.2]octane in 300 ml of acetonitrile is cooled to 10° C. At 10° C., 52.26 g (150 mmol) of 4-(3-methanesulfonyloxy-propyl)-benzoic acid benzyl ester, dissolved in 50 ml of tetrahydrofuran, is added in drops over 30 minutes while being stirred vigorously. It is stirred for two hours at 10° C. 300 ml of MTB (methyl-tert-butyl ether) is added, solid is filtered out, and the filtrate is evaporated to the dry state in a vacuum. The residue is dissolved in 500 ml of tetrahydrofuran, and 5 g of palladium (10%) on activated carbon is added thereto and hydrogenated until hydrogen absorption is completed. Then, catalyst is filtered out, it is rewashed with a little tetrahydrofuran, and the combined solutions are evaporated to the dry state in a vacuum. The residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 39.31 g (77% of theory, over two stages) of a colorless solid Elementary Analysis: Cld: C 56.47 H 5.92 Fnd: C 56.55 H 6.04

EXAMPLE 11
2,3,5-Tri-O-benzoyl-1-O-carboxymethyl-ribofuranose

A mixture that consists of 46.25 g (100 mmol) of 2,3,5-tri-O-benzoylribofuranose, 1.39 g (5 mmol) of tetrabutylammonium chloride in 400 ml of methyl-tert-butyl ether, and 82.93 g (600 mmol) of potassium carbonate is cooled to 0° C. At 0° C., 22.91 g (150 mmol) of bromoacetic acid benzyl ester is added in drops over 20 minutes while being stirred vigorously. It is stirred for one hour at 0° C. 500 ml of methyl-tert-butyl ether is added thereto, the organic phase is separated, and the aqueous phase is extracted twice with 200 ml of methyl-tert-butyl ether. The solvent of the combined organic phases is dried on sodium sulfate, dessicant is filtered out and distilled off in a vacuum. The residue is taken up in 500 ml of ethanol. 5 g of palladium (10%) on activated carbon is added thereto, and it is hydrogenated until hydrogen absorption is completed. Then, catalyst is filtered out, it is rewashed with a little ethanol and evaporated to the dry state in a vacuum. The residue is chromatographed on silica gel (mobile solvent: dichloromethane/nhexane/ethanol/acetic acid=20:5:3:0.5). The product-containing fractions are concentrated by evaporation, dissolved in 200 ml of ethyl acetate and shaken out three times with 200 ml of water. Then, the organic phase is separated and evaporated to the dry state in a vacuum.

Yield: 42.68 g (82% of theory, over two stages) of a colorless, viscous oil Elementary Analysis: Cld: C 64.61 H 4.65 Fnd: C 64.72 H 4.71

EXAMPLE 12
2,3,5-Tri-O-benzoyl-1-O-(1-amino-eth-2-yl)-ribofuranose, hydrochloride A mixture that consists of 42.1 g (100 mmol) of 2,3,5-tri-O-benzoyl-ribofuranose, 3.40 g (10 mmol) of tetrabutylammonium hydrogen sulfate and 63.94 g (600 mmol) of fine-powder sodium carbonate in 350 ml of dioxane is cooled to 10° C. At 10° C., 45.63 g (150 mmol) of N-(2-bromoethyl)-dibenzylamine, dissolved in 100 ml of benzene, is added in drops over 40 minutes while being stirred vigorously. It is stirred for three hours at 10° C., then 300 ml of benzene is added, solid is filtered out, and the filtrate is evaporated to the dry state in a vacuum. The filtrate residue is dissolved in 500 ml of ethanol, mixed with 5 g of Pearlman's catalyst (20% palladium on activated carbon) and hydrogenated until hydrogen absorption is completed. Catalyst is filtered out, it is rewashed with a little ethanol and evaporated to the dry state in a vacuum. The residue is chromatographed on silica gel (mobile solvent: dichloromethane/ethanol/triethylamine=20:2:0.1). The product-containing fractions are combined and evaporated to the dry state in a vacuum. It is taken up in absolute diethyl ether, and the product precipitates with ethereal hydrochloric acid as a hydrochloride.

Yield: 42.27 g (78% of theory, over two stages) of a colorless solid Elementary Analysis: Cld: C 62.05 H 5.21 N 2.58 Cl 6.54 Fnd: C 62.19 H 5.28 N 2.66 Cl 6.47

EXAMPLE 13
2,3,4,6-Tetra-O-benzoyl-1-O-(1-amino-prop-3-yl)-galactopyranose, hydrochloride A mixture that consists of 42.1 g (100 mmol) of 2,3,4,6-tetra-O-benzoyl-galactopyranose, 1.7 g (5 mmol) of tetrabutylammonium hydrogen sulfate and 82.93 g (600 mmol) of fine-powder potassium carbonate in 350 ml of 1,2-dimethoxyethane is cooled to 10° C. At 10° C., 47.74 g (150 mmol) of N-(3-bromopropyl)-dibenzylamine, dissolved in 100 ml of 1,2-dimethoxyethane, is added in drops over 40 minutes while being stirred vigorously. It is stirred for three hours at 10° C. 300 ml of benzene is added, solid is filtered out, and the filtrate is evaporated to the dry state in a vacuum. The residue is dissolved in 500 ml of ethanol, mixed with 5 g of Pearlman's catalyst and hydrogenated until hydrogen absorption is completed. Catalyst is filtered out, it is rewashed with a little ethanol and evaporated to the dry state in a vacuum. The residue is chromatographed on silica gel (mobile solvent: dichloromethane/ethanol/triethylamine=20:2:0.1). The product-containing fractions are combined and evaporated to the dry state in a vacuum. The residue is taken up in absolute diethyl ether, and the product precipitates by addition of ethereal hydrochloric acid as hydrochloride.

Yield: 53.14 g (77% of theory, over two stages) of a colorless solid Elementary Analysis: Cld: C 64.39 H 5.26 Cl 5.14 N 2.03 Fnd: C 64.24 H 5.34 Cl 5.21 N 2.11

EXAMPLE 14

2,3,4,6-Tetra-O-acetyl-1-O-(1-amino-hex-6-yl)-mannopyranose, hydrochloride

A mixture that consists of 34.83 g (100 mmol) of 2,3,4,6-tetra-O-acetyl-mannopyranose, 1.39 g (5 mmol) of tetrabutylammonium chloride and 35.84 g (110 mmol) of cesium carbonate in 500 ml of dioxane is cooled to 0° C. At 0° C., 60.3 g (150 mmol) of 6-bromohexylamine-N-(9-fluorenylmethoxy-carbonyl) is added in drops over 30 minutes while being stirred vigorously. It is stirred for one hour at 0° C. 300 ml of dichloromethane is added, the organic phase is separated, and it is filtered. It is evaporated to the dry state in a vacuum, and the residue is taken up in 500 ml of ethanol, 5 g of palladium (10%) on activated carbon is added thereto and hydrogenated until hydrogen absorption is completed. Then, catalyst is filtered out, it is rewashed with a little ethanol and evaporated to the dry state in a vacuum. The residue is chromatographed on silica gel (mobile solvent: dichloromethane/ethanol/triethylamine=20:2:0.1). The product-containing fractions are combined and evaporated to the dry state in a vacuum. The residue is taken up in absolute diethyl ether and mixed with ethereal hydrochloric acid. The product is obtained as hydrochloride.

Yield: 38.23 g (79% of theory, over two stages) of a colorless solid Elementary Analysis: Cld: C 49.64 H 7.08 N 2.89 Cl 7.33 Fnd: C 49.69 H 7.20 N 2.94 Cl 7.48

EXAMPLE 15

2,3,4-Tri-O--1-O-(1-amino-but-4-yl)-fucopyranose, hydrochloride benzoyl

A mixture that consists of 43.5 g (100 mmol) of 2,3,4-tri-O-benzoyl-6-deoxy-galactopyranose, 1.7 g (5 mmol) of tetrabutylammonium hydrogen sulfate, and 35.84 g (110 mmol) of cesium carbonate in 400 ml of dichloromethane is cooled to 0° C. At 10° C., 47.4 g (150 mmol) of 2-(trimethylsilyl)-ethylsulfonic acid-N-(4-bromobutyl)-amide, dissolved in 100 ml of dichloromethane, is added in drops over 30 minutes while being stirred vigorously. It is stirred for two hours at 10° C. 600 ml of dichloromethane is added, the organic phase is separated, and the aqueous phase is extracted twice with 200 ml of dichloromethane. The combined organic phases are dried on sodium sulfate. Dessicant is filtered out, and the solvent is distilled off in a vacuum. The residue is taken up in 350 ml of acetonitrile, and 52.3 g (200 mmol) of tetrabutylammonium fluoride is added as a monohydrate. It is stirred for three hours at 50° C. The solution is evaporated to the dry state, and the residue is chromatographed on silica gel (mobile solvent: dichloromethane/ethanol/triethylamine=20:2:0.1). The product-containing fractions are combined and evaporated to the dry state in a vacuum. The residue is dissolved in absolute diethyl ether and mixed with ethereal hydrochloric acid. The product is obtained as a hydrochloride.

Yield: 45.56 g (78% of theory, over two stages) of a colorless solid

Elementary Analysis:

Cld: C 63.75 H 5.87 N 2.40 Cl 6.07
Fnd: C 63.63 H 5.91 N 2.45 Cl 6.18

EXAMPLE 16

2,3,4,6-Tetra-O-pivaloyl-1-O-(3,6,9,12,15-pentaoxa-1-carboxy-hexadec-16-yl)-glucopyranose A mixture that consists of 51.66 g (100 mmol) of 2,3,4,6-tetra-O-pivaloyl-glucopyranose, 1.39 g (5 mmol) of tetrabutylammonium chloride and 63.59 g (600 mmol) of fine-powder sodium carbonate in 350 ml of dioxane is cooled to 0° C. At 0° C., 91.37 g (130 mmol) of 17-tosyloxy-3,6,9,12,15-pentaoxaheptadecanoic acid benzyl ester, dissolved in 100 ml of tetrahydrofuran, is added in drops over 50 minutes while being stirred vigorously. It is stirred for three hours at 0° C. 300 ml of dichloromethane is added, solid is filtered out, and the filtrate is evaporated to the dry state in a vacuum. The residue is taken up in 500 ml of ethanol. 5 g of palladium (10%) on activated carbon is added thereto and hydrogenated until hydrogen absorption is completed. Then, catalyst is suctioned out, it is rewashed with a little ethanol and evaporated to the dry state in a vacuum. The residue is chromatographed on silica gel (mobile solvent: dichloromethane/n hexane/ethanol/acetic acid= 20:8:5:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 61.21 g (77% of theory, over two stages) of a colorless oil Elementary Analysis: Cld: C 57.42 H 8.37 Fnd: C 57.56 H 8.29

EXAMPLE 17

2,3,4,6-Tetra-O-acetyl-1-O-(1-hydroxy-eth-2-yl)-mannopyranose

A mixture that consists of 34.83 g (100 mmol) of 2,3,4,6-tetra-O-acetyl-mannopyranose, 1.7 g (5 mmol) of tetrabutylammonium hydrogen sulfate and 82.93 g (600 mmol) of fine-powder potassium hydroxide in 350 ml of diethoxymethane is cooled to 0° C. At 0° C., 32.26 g (150 mmol) of 2-benzyloxy-ethylbromide is added in drops over 30 minutes while being stirred vigorously. It is stirred for two hours at 0° C. 300 ml of benzene is added, solid is filtered out, and the filtrate is evaporated to the dry state in a vacuum. The residue is taken up in 500 ml of ethanol. 5 g of palladium (10%) on activated carbon is added thereto and hydrogenated until hydrogen absorption is completed. Then, catalyst is suctioned out, it is rewashed with a little ethanol and evaporated to the dry state in a vacuum. The residue is chromatographed on silica gel (mobile solvent: dichloromethane/nhexane/ethanol=20:8:2). The product-containing fractions are concentrated by evaporation.

Yield: 30.60 g (78% of theory, over two stages) of a colorless, viscous oil Elementary Analysis: Cld: C 48.98 H 6.17 Fnd: C 48.84 H 6.03

EXAMPLE 18

2,3,4,6-Tetra-O-pivaloyl-1-O-carboxymethyl-mannopyranose

A mixture that consists of 51.66 g (100 mmol) of 2,3,4,6-tetra-O-pivaloyl-mannopyranose, 0.55 g (5 mmol) of tetramethylammonium chloride and 82.93 g (600 mmol) of fine-powder potassium carbonate in 350 ml of diethylene glycol dimethyl ether is cooled to 10° C. At 10° C., 36.65 g (160 mmol) of 2-bromoacetic acid benzyl ester is added in drops within 10 minutes while being stirred vigorously. It is stirred for two hours at 10° C. 250 ml of MTB (methyl-tert-butyl ether) is added, solid is filtered out, and the filtrate is evaporated to the dry state in a vacuum. The residue is taken up in 500 ml of ethanol, mixed with 5 g of palladium (10%) on activated carbon and hydrogenated until hydrogen absorption is completed. Catalyst is filtered out, it is rewashed with ethanol, and the combined solutions are evaporated to the dry state in a vacuum. The residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 45.40 g (79% of theory, over two stages) of a colorless solid Elementary Analysis: Cld: C 58.52 H 8.07 Fnd: C 58.44 H 8.18

EXAMPLE 19
2,3,4,6-Tetra-O-acetyl-1-O-(1-phenyl-1-carboxy-eth-2-yl)-mannopyranose A mixture that consists of 34.83 g (100 mmol) of 2,3,4,6-tetra-O-acetyl-mannopyranose, 1.39 g (5 mmol) of tetrabutylammonium chloride and 35.8 g (110 mmol) of finepowder cesium carbonate in 400 ml of dimethyl ether is cooled to 0° C. At 0° C., 47.88 g (150 mmol) of 2-phenyl-3-bromopropionic acid benzyl ester, dissolved in 30 ml of dimethyl ether, is added in drops over 10 minutes while being stirred vigorously. It is stirred for one hour at 0° C. 250 ml of MTB (methyl-tert-butyl ether) is added, solid is filtered out, and the filtrate is evaporated to the dry state in a vacuum. The residue is taken up in 500 ml of tetrahydrofuran. 5 g of palladium (10%) on activated carbon is added thereto and hydrogenated until hydrogen absorption is completed. Then, catalyst is filtered out, it is rewashed with a little tetrahydrofuran, the organic solutions are combined and evaporated to the dry state in a vacuum, dried, and the solvent is distilled off in a vacuum. The residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 39.22 g (79% of theory, over two stages) of a colorless solid Elementary Analysis: Cld: C 55.64 H 5.68 Fnd: C 55.81 H 5.84

EXAMPLE 20
2,3,4,6-Tetra-O-benzoyl-1-O-carboxymethyl-mannopyranose

A mixture that consists of 59.66 g (100 mmol) of 2,3,4,6-tetra-0-benzoyl-mannopyranose, 1.39 g (5 mmol) of tetrabutylammonium chloride and 15.2 g (110 mmol) of anhydrous potassium carbonate in 500 ml of diethoxymethane is cooled to 0° C. At 0° C., 36.92 g (200 mmol of 2-chloroacetic acid benzyl ester is added in drops over 20 minutes while being stirred vigorously. It is stirred for one hour at 10° C. 250 ml of methyl-tert-butyl ether is added, the organic phase is separated, it is filtered and evaporated to the dry state in a vacuum. The residue is taken up in 500 ml of ethanol and mixed with 5 g of palladium (10%) on activated carbon. It is hydrogenated until hydrogen absorption is completed. Catalyst is filtered out, it is rewashed with a little ethanol, and the combined solutions are evaporated to the dry state in a vacuum. The residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 53.82 g (82% of theory, over two stages) of a colorless, viscous oil Elementary Analysis: Cld: C 66.05 H 4.62 Fnd: C 66.21 H 4.73

EXAMPLE 21
2,3,4,6-Tetra-O-acetyl-1-O-carboxymethyl-glucopyranose

A mixture that consists of 34.83 g (100 mmol) of 2,3,4,6-tetra-O-acetyl-glucopyranose, 1.39 g (5 mmol) of tetrabutylammonium chloride and 15.22 g (100 mmol) of DBU in 300 ml of tetrahydrofuran is cooled to 0° C. At 0° C., 34.36 g (150 mmol) of 2-bromoacetic acid benzyl ester, dissolved in 40 ml of tetrahydrofuran, is added in drops over 30 minutes while being stirred vigorously. It is stirred for three hours at 0° C. 300 ml of MTB (methyl-tert-butyl ether) is added, solid is filtered out, and the filtrate is evaporated to the dry state in a vacuum. The residue is taken up in 500 ml of tetrahydrofuran. 5 g of palladium (10%) on activated carbon is added thereto and hydrogenated until hydrogen absorption is completed. Then, catalyst is filtered out, it is rewashed with a little tetrahydrofuran and evaporated to the dry state in a vacuum. The residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 31.69 g (78% of theory, over two stages) of a colorless solid Elementary Analysis: Cld: C 47.29 H 5.46 Fnd: C 47.22 H 5.61

EXAMPLE 22
2,3,4,6-Tetra-O-pivaloyl-1-O-carboxymethyl-glucopyranose

A mixture that consists of 54.1 g (100 mmol) of 2,3,4,6-tetra-O-pivaloyl-glucopyranose, 1.39 g (5 mmol) of tetrabutylammonium chloride and 11.22 g of potassium-t-butoxide (100 mmol) in 500 ml of dimethylacetamide is cooled to 0° C. At 0° C., 34.36 g (150 mmol) of 2-bromoacetic acid benzyl ester is added in drops over 20 minutes while being stirred vigorously. It is stirred for one hour at 0° C. Then, 250 ml of toluene is added thereto, solid is filtered out, it is evaporated to the dry state in a vacuum, the residue is taken up in 500 ml of ethanol, mixed with 5 g of palladium (10%) on activated carbon and hydrogenated until the hydrogen absorption is completed. Catalyst is filtered out, it is rewashed with a little ethanol and the combined organic solutions are evaporated to the dry state in a vacuum. The residue is chromatographed on silica gel (mobile solvent: dichloromethane/n-hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 47.12 g (82% of theory, over two stages) of a colorless, viscous oil Elementary Analysis: Cld: C 58.52 H 8.07 Fnd: C 58.69 H 8.19

EXAMPLE 23
2,3,4,6-Tetra-O-acetyl-1-O-carboxymethyl-glucopyranose

A mixture that consists of 34.83 g (100 mmol) of 2,3,4,6-tetra-O-acetylglucopyranose, 0.55 g (5 mmol) of tetramethylammonium chloride and 12.42 g (100 mmol) of DBN in 350 ml of benzene is cooled to 0° C. At 0° C., 34.36 g (150 mmol) of 2-bromoacetic acid benzyl ester, dissolved in 50 ml of benzene, is added in drops over 30 minutes while being stirred vigorously. It is stirred for two hours at 20° C. 250 ml of methyl-tert-butyl ether is added, solid is filtered out, and the filtrate is evaporated to the dry state in a vacuum. The residue is taken up in 500 ml of ethanol. 5 g of palladium (10%) on activated carbon is added thereto, and it is hydrogenated until hydrogen absorption is completed.

Catalyst is filtered out, it is rewashed with a little ethanol, and the combined solutions are evaporated to the dry state in a vacuum. The residue is chromatographed on silica gel (mobile solvent: dichloromethane/n-hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 31.69 g (78% of theory, over two stages) of a colorless solid Elementary Analysis: Cld: C 47.29 H 5.46 Fnd: C 47.42 H 5.60

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for production of a peracylated 1-O-glycoside formula I

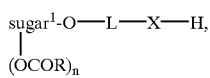
(I)

in which
sugar$^1$ is a monosaccharide that is functionalized in 1-OH-position by -L-X-H,
R is methyl, ethyl, propyl, isopropyl, tert-butyl, or phenyl,
n is 2, 3 or 4,
X is —COO— or —NH—, and
L is a straight-chain, branched, saturated or unsaturated $C_1$-$C_{30}$ carbon chain, wherein said carbon chain optionally contains 1–10 oxygen atoms, 1–3 sulfur atoms, 1–2 phenylene groups, 1–2 phenylenoxy groups, 1–2 phenylenedioxy groups, a thiophene radical, pyrimidine radical or pyridine radical, and/or wherein said carbon chain is optionally substituted by 1–3 phenyl groups, 1–3 carboxyl groups, 1–5 hydroxy groups, 1–5 O—$C_1$-$C_7$ alkyl groups, 1–3 amino groups, 1–3 $CF_3$ groups or 1–10 fluorine atoms,
or a salt thereof,
said process comprising:
reacting a peracylated 1-OH-sugar of formula II

(II)

with an alkylating reagent of formula (III)

Nu-L-X—Sg    (III), in which Nu is a nucleofuge and Sg is a protective group, in an organic solvent in the presence of a base and optionally a phase transfer catalyst at a temperature of 0–50° C., and
cleaving off the protective group, and
optionally converting the resultant reaction product into a salt.

2. A process according to claim 1, wherein said peracylated 1-OH-sugar of 1 formula II is a peracylated monosaccharide with 5 to 6 C-atoms or its deoxy compound.

3. A process according to claim 1, wherein said peracylated 1-OH-sugar of 1 formula II is peracylated glucose, mannose, galactose, ribose, arabinose, xylose, fucose or rhamnose.

4. A process according to claim 1, wherein Nu is Cl, —Br, —I, —OTs, —OMs, —OSO$_2$CF$_3$, —OSO$_2$C$_4$F$_9$ or -OSO$_2$C$_8$F$_{17}$.

5. A process according to claim 1, wherein L is selected from the group consisting of:

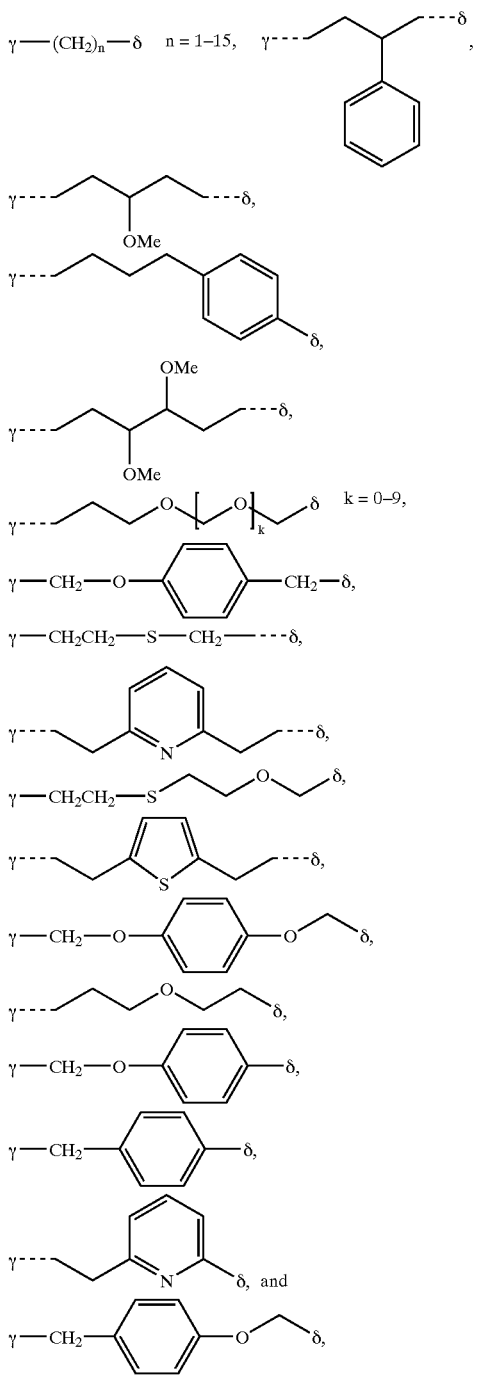

6. A process according to claim 1, wherein said organic solvent is dioxane, 1,2-dimethoxyethane, diethylene glycol dimethyl ether, diethoxymethane, tetrahydrofuran, acetonitrile, formamide, dimethylformamide dimethylacetamide, benzene, toluene, $CF_3$-benzene, hexane, cyclohexane, diethyl ether, dichloromethane, methyl-t-butyl ether, dimethyl sulfoxide, sulfolane or a mixture thereof.

7. A process according to claim 1, wherein the reaction is performed in the presence of a phase transfer catalyst selected from the group consisting of quaternary ammonium salts, phosphonium salts, and crown ethers.

8. A process according to claim 1, wherein said base is potassium carbonate, sodium carbonate, cesium carbonate, 1,8-diazabicyclo[5.4.0]undec-7-ene, 1,5-diazabicyclo[4.3.0] non-5-ene, 1,4-diazabicyclo[2.2.2]-octane, potassium-t-butoxide, sodium-t-butoxide, a mixture of cesium carbonate and potassium carbonate, or a mixture of cesium carbonate and sodium carbonate.

9. A process according to claim 1, wherein the base is added in solid form.

10. A process according to claim 1, wherein said compound of formula I is:
Carboxymethyl-2,3,4,6-tetra-O-acetyl-mannopyranose,
Carboxymethyl-2,3,4,6-tetra-O-pivaloyl-mannopyranose, or
Carboxymethyl-2,3,4,6-tetra-O-benzoyl-mannopyranose.

11. A process according to claim 1, wherein the base is added in liquid form.

12. A process according to claim 1, wherein the reaction is carried out at temperatures of 0° C. to room temperature.

13. A process according to claim 7, wherein said phase transfer catalyst is a quaternary ammonium salt having four hydrocarbon groups that are the same or different and are selected from the group consisting of methyl, ethyl, propyl, isopropyl, butyl, and isobutyl.

14. A process according to claim 7, wherein said phase catalyst is $N(butyl)_4^+$-$Cl^-$, $N(butyl)_4^+$-$HSO_4^-$, or $N(methyl)_4^+$-$Cl^-$.

15. A process according to claim 1, wherein X is —COO— and Sg is an acid protective group selected from the group consisting of methyl, ethyl, benzyl, tert-butyl, allyl, and silyl.

16. A process according to claim 1, wherein said compound of formula I is:
2,3,4,6-Tetra-O-acetyl-1-O-carboxymethyl-mannopyranose,
2,3,4,6-Tetra-O-benzoyl-1-O-carboxymethyl-mannopyranose,
2,3,4,6-Tetra-O-pivaloyl-1-O-(5-carboxypentyl)-mannopyranose,
2,3,4,6-Tetra-O-acetyl-1-O-(1-phenyl-1-carboxy-eth-2-yl)-mannopyranose,
2,3,4,6-Tetra-O-benzoyl-1-O-carboxymethyl-mannopyranose,
2,3,4,6-Tetra-O-acetyl-1-O-(4-carboxybutyl)-glucopyranose,
2,3,4,6-Tetra-O-pivaloyl-1-O-carboxymethyl-glucopyranose,
2,3,4,6-Tetra-O-acetyl-1-O-(10-carboxydecyl)-glucopyranose,
2,3,4,6-Tetra-O-acetyl-1-O-carboxymethyl-galactopyranose,
2,3,4,6-Tetra-O-acetyl-1-O-[1-(4-carboxy)-phenyl-prop-3-yl-galactopyranose,
2,3,5-Tri-O-benzoyl-1-O-carboxymethyl-ribofuranose,
2,3,5-Tri-O-benzoyl-1-O-(1-amino-eth-2-yl)-ribofuranose, hydrochloride,
2,3,4,6-Tetra-O-benzoyl-1-O-(1-amino-prop-3-yl)-galactopyranose, hydrochloride,
2,3,4,6-Tetra-O-acetyl-1-O-(1-amino-hex-6-yl)-mannopyranose, hydrochloride
2,3,4-Tri-O-1-O-(1-amino-but-4-yl)-fucopyranose, hydrochloride benzoyl,
2,3,4,6-Tetra-O-pivaloyl-1-O-(3,6,9,12,15-pentaoxa-1-carboxy-hexadec-16-yl) glucopyranose,
2,3,4,6-Tetra-O-acetyl-1-O-(1-hydroxy-eth-2-yl)-mannopyranose,
2,3,4,6-Tetra-O-pivaloyl-1-O-carboxymethyl-mannopyranose,
2,3,4,6-Tetra-O-acetyl-1-O-(1-phenyl-1-carboxy-eth-2-yl)-mannopyranose,
2,3,4,6-Tetra-O-benzoyl-1-O-carboxymethyl-mannopyranose,
2,3,4,6-Tetra-O-acetyl-1-O-carboxymethyl-glucopyranose,
2,3,4,6-Tetra-O-pivaloyl-1-O-carboxymethyl-glucopyranose, or
2,3,4,6-Tetra-O-acetyl-1-O-carboxymethyl-glucopyranose.

17. A process according to claim 1, wherein L is —$CH_2$—.

18. A compound wherein said compound is:
Carboxymethyl-2,3,4,6-tetra-O-acetyl-mannopyranose,
Carboxymethyl-2,3,4,6-tetra-O-pivaloyl-mannopyranose, or
Carboxymethyl-2,3,4,6-tetra-O-benzoyl-mannopyranose.

* * * * *

UNITED STATES PATENT AND TRADEMARK OFFICE
CERTIFICATE OF CORRECTION

PATENT NO. : 6,831,164 B2
DATED : December 14, 2004
INVENTOR(S) : Johannes Platzek et al.

It is certified that error appears in the above-identified patent and that said Letters Patent is hereby corrected as shown below:

<u>Title page,</u>
Insert Item -- [30]    Foreign Application Priority Data
      July 11, 2001   DE 10135098.8 --

<u>Column 17,</u>
Line 23, "reads "glycoside formula I", should read -- glycoside of formula I --

<u>Column 19,</u>
Lines 33-34, reads "phase catalyst", should read -- phase transfer catalyst --

Signed and Sealed this

Tenth Day of May, 2005

JON W. DUDAS
*Director of the United States Patent and Trademark Office*